US010753865B2

(12) United States Patent
    Stambaugh

(10) Patent No.: US 10,753,865 B2
(45) Date of Patent: *Aug. 25, 2020

(54) IDENTIFYING TARGETED GASEOUS CHEMICAL COMPOUND

(71) Applicant: Itron, Inc., Liberty Lake, WA (US)

(72) Inventor: Mark A. Stambaugh, Liberty Lake, WA (US)

(73) Assignee: Itron, Inc., Liberty Lake, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/235,384

(22) Filed: Dec. 28, 2018

(65) Prior Publication Data

US 2019/0137391 A1    May 9, 2019

Related U.S. Application Data

(63) Continuation of application No. 15/806,714, filed on Nov. 8, 2017, now Pat. No. 10,168,276.

(51) Int. Cl.
    *G01N 21/25*      (2006.01)
    *G01N 21/3518*    (2014.01)
    *G01N 33/00*      (2006.01)
    *G01N 21/3504*    (2014.01)
    *G01N 21/03*      (2006.01)

(52) U.S. Cl.
    CPC ..... *G01N 21/3518* (2013.01); *G01N 21/0303* (2013.01); *G01N 21/3504* (2013.01); *G01N 33/0047* (2013.01); *G01N 2201/062* (2013.01); *G01N 2201/0662* (2013.01); *G01N 2201/0686* (2013.01)

(58) Field of Classification Search
    CPC .... G01N 21/35; G01N 21/3518; G01N 33/00; G01N 21/64; G01N 21/65; G01J 3/02; G01J 3/10; G01J 3/18
    See application file for complete search history.

(56) References Cited

U.S. PATENT DOCUMENTS

| 3,676,004 | A | 7/1972 | Prugger et al. |
| 4,471,220 | A | 9/1984 | Perry et al. |
| 4,958,076 | A | 9/1990 | Bonne et al. |
| 5,002,391 | A | 3/1991 | Wolfrum et al. |
| 5,544,186 | A | 8/1996 | Sauer et al. |

(Continued)

FOREIGN PATENT DOCUMENTS

| CN | 105225404 | 1/2016 |
| GB | 2163251 | 2/1986 |

OTHER PUBLICATIONS

PCT Search Report and Written Opinion dated Feb. 14, 2019 for PCT Application No. PCT/US2018/059847, 18 pages.

*Primary Examiner* — Abdullahi Nur
(74) *Attorney, Agent, or Firm* — Lee & Hayes, P.C.

(57) ABSTRACT

Systems and methods for verifying that light absorption is caused by a targeted gaseous chemical compound. A first transmittance of light, either generated at, or filtered to, a first wavelength range and a second transmittance of light, either generated at, or filtered to, a second wavelength range are measured by first and second photon detectors. A ratio of the first and second measured transmittance is determined and that ratio is compared to a transmittance ratio associated with a targeted gaseous chemical compound to verify that the light absorption is caused by the targeted gaseous chemical compound.

20 Claims, 7 Drawing Sheets

(56) References Cited

U.S. PATENT DOCUMENTS

| | | | |
|---|---|---|---|
| 6,545,278 B1 | 4/2003 | Mottier et al. | |
| 10,168,276 B1* | 1/2019 | Stambaugh | G01N 21/3518 |
| 2006/0226348 A1 | 10/2006 | Abreu et al. | |
| 2006/0278829 A1 | 12/2006 | Ll et al. | |
| 2014/0009751 A1* | 1/2014 | Pezzaniti | G01N 33/2835 |
| | | | 356/70 |

* cited by examiner

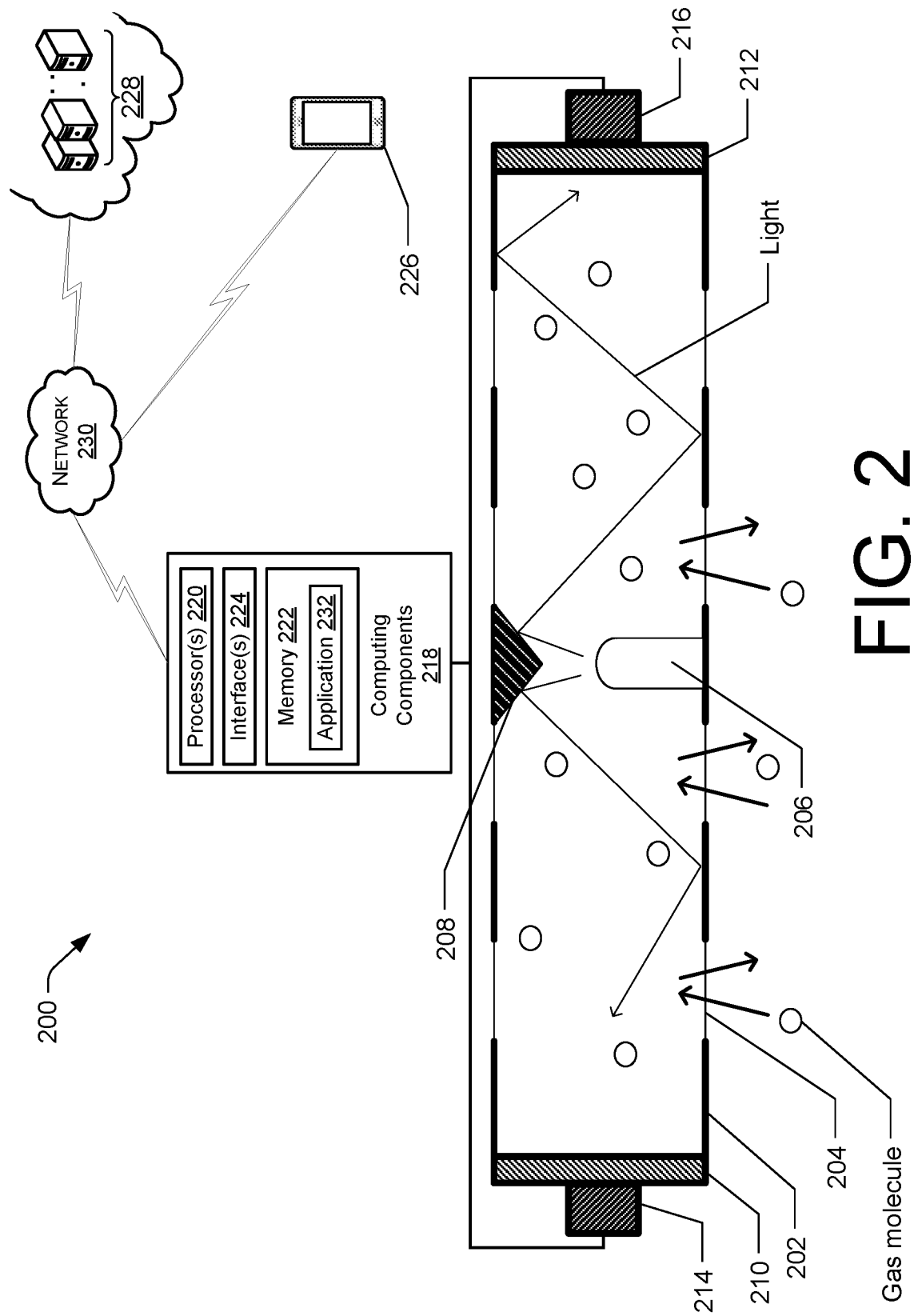

IDENTIFYING TARGETED GASEOUS CHEMICAL COMPOUND

RELATED APPLICATIONS

This application claims priority to and is a continuation of U.S. patent application Ser. No. 15/806,714, filed on Nov. 8, 2017, the entire contents of which are incorporated herein by reference.

BACKGROUND

Unwanted and/or unsafe gases may be present in residential and/or commercial environments, such as from gas leaks. Such gases may be detected via mass spectrometers, which are expensive and bulky. Other detectors are designed to detect a particular gas, but they do so by measuring absorption of light at a particular wavelength, which does not accurately verify that a targeted gaseous chemical compound caused the absorption, leading to inaccurate measurements and false positive detections.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

FIG. 2 illustrates a schematic diagram of components of an example system for targeted gaseous chemical compound verification.

DETAILED DESCRIPTION

Figure 1A:
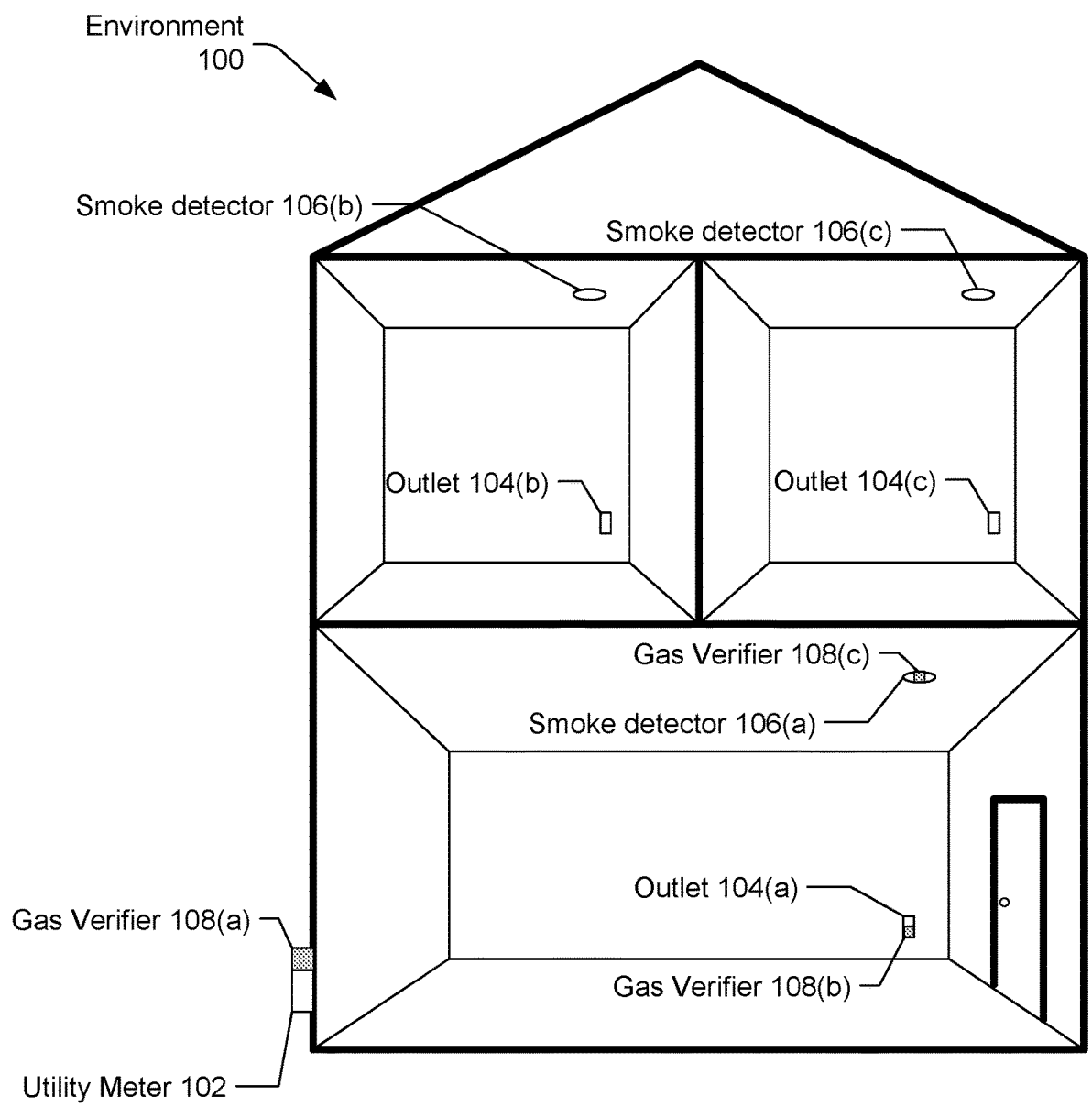
FIG. 1A illustrates a schematic diagram of an example environment that includes an example system for targeted gaseous chemical compound verification.

Systems and methods for verifying that a targeted gaseous chemical compound is a cause of light absorption are described herein. In both residential and commercial environments, one or more gaseous chemical compounds may be considered hazardous or undesirable. A residential environment such as a home may draw energy from one or more sources, and/or residential environments may include volatile compounds such as butane propellants in aerosol cans used, for example, with hair spray and/or deodorant. Those sources of energy may be, for example, natural gas, propane, alcohol, etc. While these fuel sources may be useful, apparatuses used to transport, regulate, measure, and/or burn these fuel sources may leak into and/or around the home. Gases corresponding to these fuel sources may be hazardous to humans residing in the home by way of inhalation and/or because of the flammable nature of the gases. As such, a gas detector that accurately verifies that light absorption corresponds to a targeted gaseous chemical compound within the home may be utilized.

The gas verification systems described herein may include a light source and one or more optical filters. The light source may be, for example, a tungsten bulb that produces light in the infrared light spectrum. Each of the optical filters may be tuned or otherwise configured to allow a particular wavelength range of the light to pass through the filter to a photon detector, such as, for example, a photodiode. Continuing with the example of a home environment from above, the home may utilize natural gas for one or more purposes such as powering a range, a fireplace, a water heater, and/or a furnace, for example. A primary gaseous chemical compound of natural gas is methane, and a gas detector that can accurately verify that methane is present and other gases or conditions in the mixture are not affecting the verification/measurement of methane may be desired.

Methane absorbs infrared light at multiple wavelengths and has two dominant absorption bands of infrared light at or, in a range around, 3020 $cm^{-1}$ and at or around 1306 $cm^{-1}$. Thus, in this example where methane is the gaseous chemical compound to be detected, one of the optical filters may be configured to allow a wavelength range of light around 3020 $cm^{-1}$ to pass from the light source to a photon detector. Another of the optical filters may be configured to allow another wavelength range of light around 1306 $cm^{-1}$ to pass from the light source to the photon detector or another photon detector. The photon detectors may measure absorption of the light by the methane. If the photon detectors measure an absorption of light at the two wavelength ranges described above, then a ratio of the amount of absorbed light at the first wavelength range to the amount of absorbed light at the second wavelength range may be determined. In examples, the ratio may be utilized to accurately verify that light absorption is caused by the targeted gaseous chemical compound and/or other gases or conditions in the mixture are not affecting the verification/measurement of the targeted gaseous chemical compound. In further examples, the ratio may be utilized to verify that light absorbance by a gas is not caused by a targeted gaseous chemical compound.

In examples, the absorption data may be utilized to determine a concentration of methane detected at the gas detector and one or more actions may be taken when the concentration exceeds a threshold concentration. The actions may include outputting an audible alarm, sending message data indicating that methane has been detected to a mobile device, and/or sending data to a utility and/or monitoring company that responds to information about the detected methane.

The gas detectors described herein may alternatively include two or more light emitting diodes (LEDs) that are configured to produce light at certain wavelength ranges. Continuing with the example of methane from above, a first LED may be configured to emit light at a wavelength range at or around 3020 $cm^{-1}$, and a second LED may be configured to emit light at a wavelength range at or around 1306 $cm^{-1}$. A photon detector may be utilized for each LED or for both LEDs and may measure absorption of light produced by the LED by one or more gaseous chemical compounds. The one or more photon detectors may measure absorption as described above and a ratio of absorption at the first wavelength range to absorption at the second wavelength range may be determined. That ratio may be compared to a predetermined absorption ratio for methane and, if the detected ratio matches or substantially matches the predetermined absorption ratio, it may be determined that methane is the primary compound present that is affecting the measurement. The concentration of the detected methane may be determined from the absorption data, and when the detected concentration meets or exceeds a threshold concentration, one or more actions may be taken. Those actions may include producing an alarm, sending a notification to a mobile device, or sending information about the detection to a remote source such as a utility or monitoring company.

While methane has been used in the above examples, it should be understood that the one or more optical filters and/or the LEDs may be tuned to wavelength ranges that are characteristic of any gaseous chemical compound. The one or more photon detectors that measure absorption may generate data representing that absorption and may send that data to one or more processors configured with computer-readable media that may determine the absorption and/or transmittance of light at the wavelength ranges and may determine the ratio of absorption and/or transmittance. The one or more processors and computer-readable media may be disposed in the gas detector itself, may be located remotely from the gas detector, or both.

Additional details are described below with reference to several example embodiments.

FIG. 1A illustrates a schematic diagram of an example environment 100 that includes a gas detection system. The environment 100 depicts a multi-level dwelling, such as a home. While environment 100 depicted in FIG. 1A is a residential environment, it should be understood that the gas detection systems described herein may be disposed at commercial environments as well, indoors or outdoors. The environment 100 includes a utility meter 102, such as a natural gas meter that measures usage of natural gas at the environment 100. The environment 100 also includes one or more outlets 104(a)-(c) situated in the rooms of the environment 100. The one or more outlets 104(a)-(c) may be, for example, electric outlets and/or gas outlets. The environment 100 also includes one or more smoke and/or carbon monoxide detectors 106(a)-(c) situated in the rooms of the environment 100.

The gas verification systems described herein, such as gas verifiers 108(a)-(c), may be situated at or near one or more of the utility meter 102, the outlets 104(a)-(c), and/or the smoke and/or carbon monoxide detectors 106(a)-(c). In examples, when the gas verification system 108(a) is positioned at or near the utility meter 102, the gas verification system 108(a) may verify that light absorption is caused by a targeted gas and/or other gases are not affecting the verification measurements of the targeted gas. When the gas verification system 108(b)-(c) is positioned at or near one or more outlets 104(a)-(c) and/or at or near one or more smoke and/or carbon monoxide detectors 106(a)-(c), the gas verification system 108(b)-(c) may verify that a detected gas is a targeted gas and/or is not a targeted gas that may be leaking from pipes situated within the environment 100 and/or from heating mechanisms that utilize the gas as a fuel source, such as a fireplace, range, water heater, and/or furnace. In these examples, placement of the gas verification system 108(b) at or near the outlets 104(a)-(c) of a given room in the environment 100 may be desirable when the gas of interest is heavier than air and, thus, sinks to the bottom of the room. Placement of the gas verification system 108(c) at or near smoke and/or carbon monoxide detectors 106(a)-(c) may be desirable when the gas of interest is lighter than air and, thus, floats to the top of the room. The gas verification systems 108(a)-(c) described herein may be placed at one or more of the locations described above, and/or the gas verification system 108(a)-(c) may be placed elsewhere in the environment 100, such as, for example, at or near a range, an oven, a fireplace, a hot water heater, a furnace, and/or other heating elements located in the environment 100.

When the gas verification systems 108(a)-(c) described herein are provided at a commercial environment, the systems may be positioned at or near locations where people are commonly located, such as offices and communal areas, and/or at or near heating elements present in the commercial environment, and/or where gas lines are connected to the commercial environment, for example.

FIG. 2 illustrates a schematic diagram of an example system 200 for verifying that absorption of light is caused by or is not caused by a targeted gaseous chemical compound. System 200 includes a cross-sectional view of a portion of a gas verification system along with one or more computing components, described below. System 200 may include a housing 202, which may have one or more apertures 204 that may allow gas molecules to pass from the exterior of the housing 202 to the interior of the housing 202, and vice versa. The system 200 may also include a light source 206, which may produce light within the interior of the housing 202. The light source 206 may produce light in any electromagnetic wavelength, which may include, for example, the visible, infrared, ultraviolet, and/or x-ray ranges. In examples, the light source 206 may include a tungsten filament that, when electrical current is applied to the tungsten filament, produces the light. The light source 206 may have a bulb with the filament disposed within the bulb, and a gas, such as, for example, argon, xenon, and/or krypton may fill all or a portion of the bulb. The light source 206 may additionally, or alternatively, include a flame, a laser, and/or a high intensity discharge light. The system 200 may also include a reflector 208, which may reflect light produced by the light source 206 away from the light source and toward at least one end of the housing 202.

The system 200 may additionally include a first optical filter 210 and a second optical filter 212. The first optical filter 210 may be situated on one end of the housing 202 while the second optical filter 212 may be situated on an opposing end of the housing 202, as shown in FIG. 2. In other examples, the optical filters may be situated at various angles from the light source 206. For example, the first optical filter 210 may be situated at a 90° angle from the second optical filter 212 with respect to the light source 206. In other examples, the first optical filter 210 may be situated substantially adjacent to the second optical filter 212. In yet other examples, the first optical filter 210 and the second optical filter 212 may be the same optical filter. The optical filters described herein may be configured to selectively allow passage of wavelength ranges of the light produced by the light source 206 to one or more photon detectors and/or prevent passage of wavelength ranges of the light. The optical filters 210 and 212 may be composed of glass and/or polymer that may be dyed and/or coated with a material that permits the selected wavelength range of light to pass through the optical filter while hindering, attenuating, or preventing other wavelength ranges of light from passing through the optical filter. The optical filters 210 and 212 may be absorptive filters, which may absorb light other than the selected wavelength range of light. Additionally, or alternatively, the optical filters may be dichroic filters, which may reflect light other than the selected wavelength range of light. In the example provided in FIG. 2, there are two optical filters 210 and 212. However, in other examples, one or more than two optical filters may be present.

The system 200 may additionally include a first photon detector 214 and a second photon detector 216. The first photon detector 214 may be disposed adjacent to the first optical filter 210 and may receive filtered light that passes through the first optical filter 210. The second photon detector 216 may be disposed adjacent to the second optical filter 212 and may receive filtered light that passes through the second optical filter 212. In other examples, the system 200 may include only one photon detector that is configured to perform the functions described with respect to the first photon detector 214 and the second photon detector 216. The photon detectors 214 and 216 may receive the filtered light and convert that light to a current. For example, when photons of the light hit a photon detector, those photons may be absorbed by at least a portion of the photon detector and a corresponding current may be generated proportional to the amount of light absorbed by the photon detector. In examples, the optical filters 210 and 212 described herein may be a component of the photon detectors 214 and 216. In other examples, the optical filters 210 and 212 may be a separate component from the photon detector 214 and 216. The photon detectors described herein may be semiconductor devices that convert light to current. Or the semiconductor properties in the photon detectors can be sensitive to specific wavelengths.

The current and/or signal generated by the photon detectors 214 and 216 may be transmitted to one or more computing components 218 of the system 200. The computing components 218 may include one or more processors 220. As used herein, a processor, such as processor(s) 220, may include multiple processors and/or a processor having multiple cores. The processor may be configured with multitasking functionality (e.g., a real-time multitasking operating system) and be able to simultaneously process input from a plurality of photon detectors and/or other light-frequency detectors. Further, the processors may comprise one or more cores of different types. For example, the processors may include application processor units, graphic processing units, and so forth. In one implementation, the processor may comprise a microcontroller and/or a microprocessor. The processor(s) 220 may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, the processor(s) 220 may possess its own local memory, which also may store program components, program data, and/or one or more operating systems.

The computing components 218 may also include memory 222. Memory 222 may include volatile and non-volatile memory, removable and non-removable media implemented in any method or technology for storage of information, such as computer-readable instructions, data structures, program component, or other data. Such memory 222 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 222 may be implemented as computer-readable storage media ("CRSM"), which may be any available physical media accessible by the processor(s) 220 to execute instructions stored on the memory 222. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Further, functional components may be stored in the respective memories, or the same functionality may alternatively be implemented in hardware, firmware, application specific integrated circuits, field programmable gate arrays, or as a system on a chip (SoC). In addition, while not illustrated, the memory 222 discussed herein may include at least one operating system (OS) component that is configured to manage hardware resource devices such as the network interface(s), the I/O devices of the respective apparatuses, and so forth, and provide various services to applications, such as application 232, or components executing on the processors.

The computing components 218 may also include one or more network interfaces 224, which may enable communications between the system 200, one or more devices 226, and/or a remote system 228, as well as other networked devices. Such network interface(s) 224 can include one or more network interface controllers (NICs) or other types of transceiver devices to send and receive communications over a network, such as network 230.

For instance, the network interface(s) 224 may include a personal area network (PAN) component to enable communications over one or more short-range wireless communication channels. For instance, the PAN component may enable communications compliant with at least one of the following standards IEEE 802.15.4 (ZigBee), IEEE 802.15.1 (Bluetooth), IEEE 802.11 (WiFi), or any other PAN communication protocol. Furthermore, the network interface(s) 224 may include a wide area network (WAN) component to enable communication over a wide area network. The network 230 may represent an array of wired networks, wireless networks, such as WiFi, or combinations thereof. In another to the computing components 218 shown in FIG. 2, one or more additional components to facilitate the functionality of the computing components 218 as described herein may be provided. For example, one or more analog-to-digital converters and/or one or more digital-to-analog converters may be in communication with one or more of the computing components 218. The converters may convert analog signals to digital signals, such as, for example, when the analog signal associated with the measurement of light absorption at the photon detectors is to be converted to a digital signal, which may then be utilized by the computing components 218 and/or sent to a remote system 228.

In some instances, the remote system 228 may be local to an environment associated with the system 200. For instance, the remote system 228 can be located within a home or business associated with the system 200. In some instances, some or all of the functionality of the remote system 228 may be performed by one or more of the computing components 218.

An example of how the system 200, or components thereof, may accurately verify that light absorption is caused by the targeted gaseous chemical compound and/or that other gases or conditions in the mixture are not affecting the verification/measurement of the targeted gaseous chemical compound as provided below. In this example, the system 200 is configured to verify that light absorbance is caused by methane or is not caused by methane. However, it should be appreciated that this example is for purposes of illustration and the system 200 may be configured to verify that absorbance is caused by a gas other than methane and/or a mixture of gases that may or may not include methane and other gases. In instances where the system 200 is configured to verify a mixture of gases, the system 200 may be calibrated to monitor for specific gas combinations. In this example, the light source 206 may produce light in the infrared range. The light may emit from the light source 206 and travel within the interior of the housing 202 from the light source 206 to opposing ends of the housing 202. At least a portion of the light may hit the reflector 208, which may reflect the light towards the opposing ends of the housing 202. The optical filters 210 and 212 may be disposed on the opposing ends of the housing 202 and may filter the light emitted from the light source 206 such that only a predetermined wavelength range of light passes through each optical filter. For example, when the system 200 is configured to verify that absorbance is caused by or is not caused by methane, the first optical filter 210 may be configured to allow a first wavelength range of the light to pass through the first optical filter 210, while the second optical filter 212 may be configured to allow a second wavelength range of the light to pass through the second optical filter 212. An example infrared absorption spectrum for the absorbance of methane is provided at FIG. 1B to aid in this example.

Figure 1B:
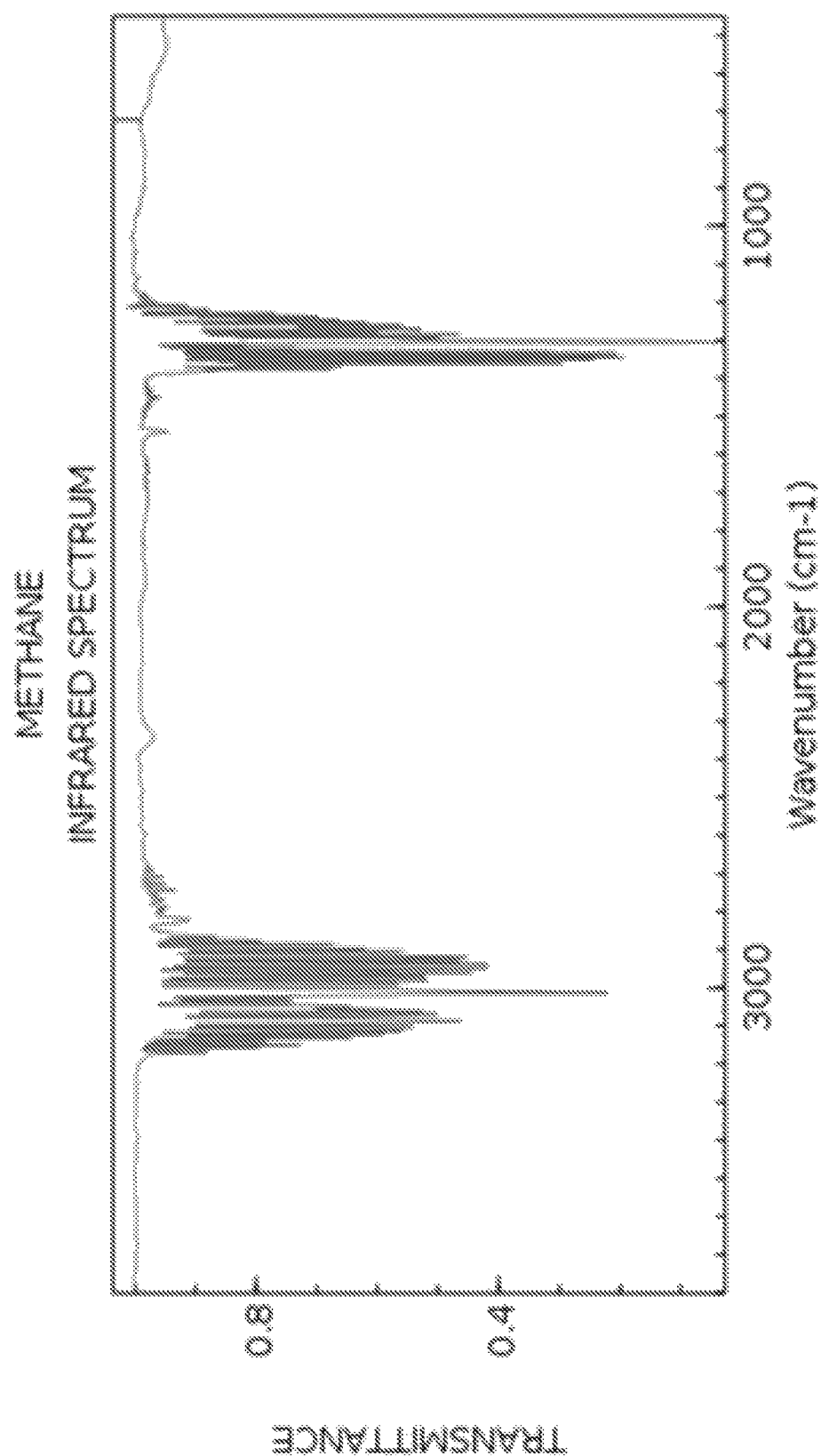
FIG. 1B illustrates an example infrared absorption spectrum for a sample of methane gas.

As shown in the example from FIG. 1B, methane absorbs light at a first wavelength range between about 3200 $cm^{-1}$ and about 2800 $cm^{-1}$. Methane also absorbs light at a second wavelength range between about 1250 $cm^{-1}$ and 1400 $cm^{-1}$. The example infrared absorption spectrum shows wavenumbers on the x-axis and transmittance on the y-axis. The transmittance scale is from 1.0, representing 100% of the light being transmitted to the photon detector (or no absorption), to 0.0, representing 0% of the light being transmitted to the photon detector (or complete absorption). Given the above, the first optical filter 210 may be configured to transmit light in the first wavelength range and prevent other wavelengths of the light from being transmitted to the first photon detector 214. Additionally, the second optical filter 212 may be configured to transmit light in the second wavelength range and prevent other wavelengths of the light from being transmitted to the second photon detector 216. In other examples, the wavelength ranges provided above for the first wavelength range may be from about 3150 $cm^{-1}$ to about 2850 $cm^{-1}$, from about 3100 $cm^{-1}$ to about 2900 $cm^{-1}$, from about 3050 $cm^{-1}$ to about 2950 $cm^{-1}$, from about 3050 $cm^{-1}$ to about 3000 $cm^{-1}$, from about 3015 $cm^{-1}$ to about 3030 $cm^{-1}$, from about 3020 $cm^{-1}$ to about 3025 $cm^{-1}$, from about 2900 $cm^{-1}$ to about 2950 $cm^{-1}$, from about 2900 $cm^{-1}$ to about 2925 $cm^{-1}$, or from about 2900 $cm^{-1}$ to about 2915 $cm^{-1}$. The wavelength ranges provided above for the second wavelength range may be from about 1300 $cm^{-1}$ to about 1350 $cm^{-1}$, from about 1300 $cm^{-1}$ to about 1325 $cm^{-1}$, or from about 1300 $cm^{-1}$ to about 1315 $cm^{-1}$, for example.

In this example, when only atmospheric air is present within the housing 202, the transmittance of the light from the light source 206, through the optical filters 210 and 212, and received at the first photon detector 214 and the second photon detector 216 may be at or near 100%. However, when molecules of methane enter the housing 202 through the one or more apertures 204, the light from the light source 206 may hit one or more of the methane gas molecules, which may absorb the wavelengths of the light characteristic of methane, as described above. Due to the absorption of the light by the methane molecules, the transmittance of the light as detected by the photon detectors 214 and 216 may decrease such that less than 100% of the light corresponding to the first wavelength range and the second wavelength range is received at the photon detectors 214 and 216.

The photon detectors 214 and 216 may transmit an analog current and/or voltage corresponding to the light transmittance to the computing components 218 of the system 200. This analog current and/or voltage may be described as data, which may include the analog current and/or voltage itself and/or may include a digital signal corresponding to the analog current and/or voltage. The digital signal may be generated by, for example, an analog-to-digital converter. The one or more processors 220 may execute instructions stored on the memory 222 to perform operations using the data received from the photon detectors 214 and 216. For example, the operations may include receiving, from the first photon detector 214, first data indicating a first transmittance of the light at the first wavelength range. The first data may be based at least in part on a decreased number of photons hitting the first photon detector 214 and a corresponding reduction in current generated by the first photon detector 214. The operations may also include receiving, from the second photon detector 216, second data indicating a second transmittance of the light at the second wavelength range. The second data may be based at least in part on a decreased number of photons hitting the second photon detector 216 and a corresponding reduction in current generated by the second photon detector 216.

The operations may further include determining that a ratio of the first transmittance to the second transmittance corresponds to a transmittance ratio associated with a targeted gaseous chemical compound, which is methane in this example. The transmittance ratio of a first wavelength range of light to a second wavelength range of light may be gas dependent and/or wavelength range dependent. For example, the transmittance ratio of methane may differ from the transmittance ratio of other gaseous chemical compounds. To illustrate, methane may absorb infrared light at dominant absorption bands around 3020 $cm^{-1}$ and 1306 $cm^{-1}$. These dominant absorption bands may differ for gases other than methane. The transmittance ratio of light transmission at two dominant absorption bands may be, for example, 10:1, 9:1, 8:1, 7:1, 6:1, 5:1, 4:1, 3:1, or 2:1. While certain exemplary absorption bands are mentioned as relating to particular wavelengths, it should be appreciated that physical characteristics of the system will introduce certain variance. Based at least in part on this variance, the reference ratio may include a range of values that account for measurement tolerances.

The operations may further include verifying that methane is the cause of the light absorption based at least in part on determining that the detected ratio matches or substantially matches the transmittance ratio associated with methane. In examples, additional data, such as humidity data and temperature data may be utilized to compensate for humidity and temperature differences. In further examples, the operations may include determining the concentration of methane in the housing 202 using the transmittance data, as received from the first photon detector 214 or the second photon detector 216, and determining that methane is present in the housing 202 based at least in part on the concentration being at or above a threshold concentration.

In the example provided with respect to FIG. 2, the computing components 218 may be part of the gas verifier and may be located at the environment that the gas is detected at. In other examples, some or all of the computing components 218 may be located at a remote location, such as remote system 228. As such, some or all of the operations described above with respect to FIG. 2 may be performed locally at the gas detector or at the remote system 228.

Figure 3:
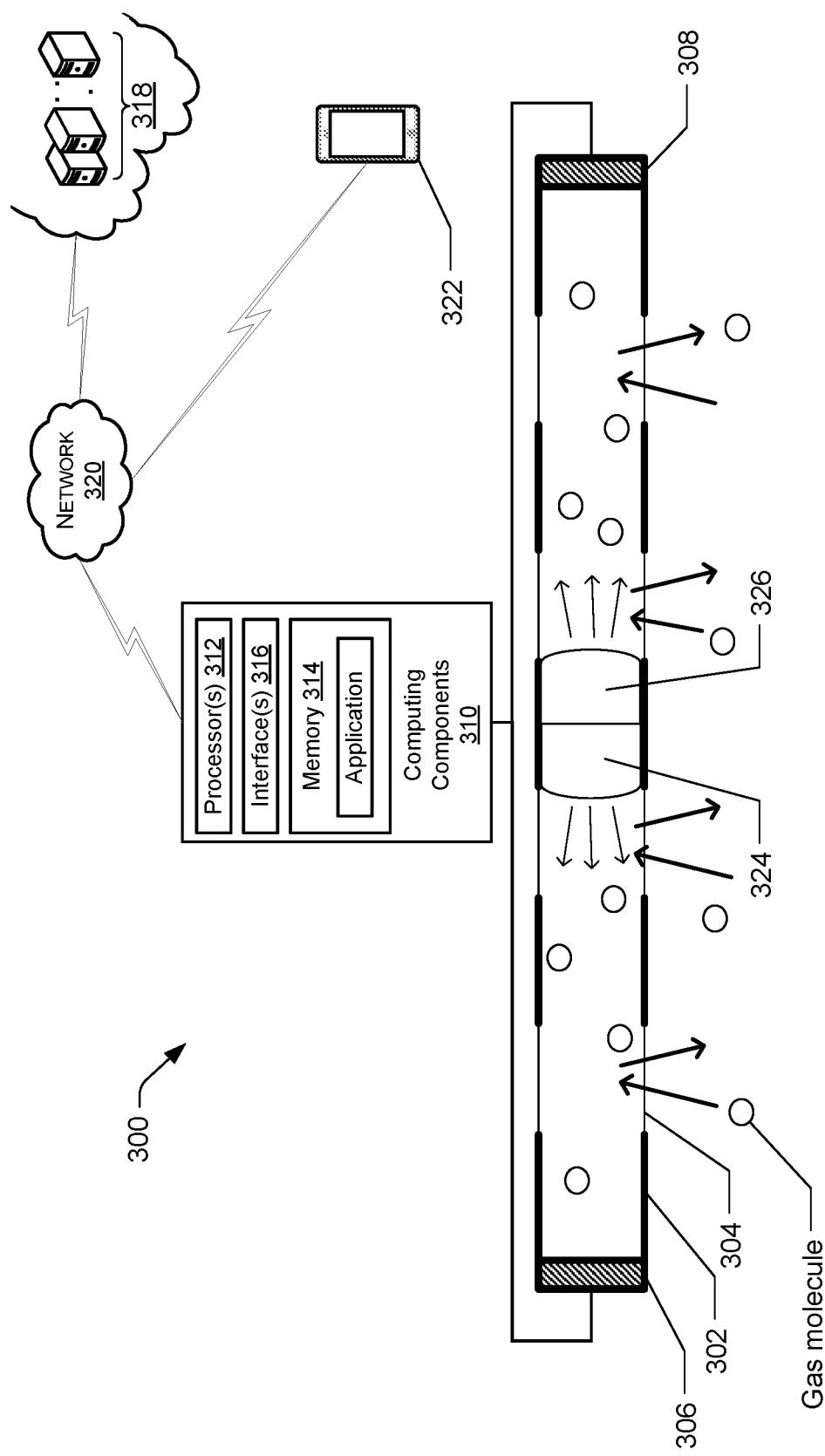
FIG. 3 illustrates a schematic diagram of components of another example system for targeted gaseous chemical compound verification.

FIG. 3 illustrates a schematic diagram of another example system 300 for verifying that light absorption is caused by or is not caused by a targeted gaseous chemical compound. System 300 includes a cross-sectional view of a portion of a gas verification system along with one or more computing components, described below. System 300 may include the same or similar components to those described with respect to FIG. 2. For example, the system 300 may include a housing 302, one or more apertures 304, a first photon detector 306, a second photon detector 308, and computing components 310. The computing components 310 may include one or more processors 312, memory 314, and one or more network interfaces 316. The computing components 310 may communicate with a remote system 318 via a network 320 and/or other devices 322.

In addition to the components described above, the system 300 may also include a first light emitting diode (LED) 324 and a second LED 326. The first LED 324 may be configured to emit light at a first wavelength range, while the second LED 326 may be configured to emit light at a second wavelength range. Using the example provided with respect to FIG. 2 where the gas verification system is configured to detect methane, the first LED 324 and the second LED 326 may be configured to emit light at wavelength ranges corresponding to characteristic absorption bands of methane. For example, the wavelength ranges for which the first LED 324 may be configured to a variety of ranges, such as from about 3150 $cm^{-1}$ to about 2850 $cm^{-1}$, from about 3100 $cm^{-1}$ to about 2900 $cm^{-1}$, from about 3050 $cm^{-1}$ to about 2950 $cm^{-1}$, from about 3050 $cm^{-1}$ to about 3000 $cm^{-1}$, from about 3015 $cm^{-1}$ to about 3030 $cm^{-1}$, from about 3020 $cm^{-1}$ to about 3025 $cm^{-1}$, from about 2900 $cm^{-1}$ to about 2950 $cm^{-1}$, from about 2900 $cm^{-1}$ to about 2925 $cm^{-1}$, or from about 2900 $cm^{-1}$ to about 2915 $cm^{-1}$. The wavelength ranges for which the second LED 326 may be configured may be from about 1300 $cm^{-1}$ to about 1350 $cm^{-1}$, from about 1300 $cm^{-1}$ to about 1325 $cm^{-1}$, or from about 1300 $cm^{-1}$ to about 1315 $cm^{-1}$, for example.

The first LED 324 and the second LED 326 may produce light at one or more of the wavelength ranges described above, for example. In this example, when only atmospheric air is present within the housing 302, the transmittance of the light from the first LED 324 and received at the first photon detector 306 may be at or near 100%. Likewise, the transmittance of the light from the second LED 326 and received at the second photon detector 308 may be at or near 100%. However, when molecules of methane enter the housing 302 through the one or more apertures 304, the light from the first LED 324 and the second LED 326 may interact with one or more of the methane gas molecules, which may absorb the wavelengths of the light characteristic of methane, as described above. Due to the absorption of the light by the methane molecules, the transmittance of the light as detected by the photon detectors 306 and 308 may decrease such that less than 100% of the light corresponding to the first wavelength range and the second wavelength range is received at the photon detectors 306 and 308.

The photon detectors 306 and 308 may transmit data corresponding to the light transmittance to the computing components 310 of the system 300. The one or more processors 312 may execute instructions stored on the memory 314 to perform operations using the data received from the photon detectors 306 and 308. For example, the operations may include receiving, from the first photon detector 306, first data indicating a first transmittance of the light at the first wavelength range. The first data may be based at least in part on a decreased number of photons hitting the first photon detector 306 caused by an increase in absorbed photons by the gas and a corresponding reduction in current generated by the first photon detector 306. The operations may also include receiving, from the second photon detector 308, second data indicating a second transmittance of the light at the second wavelength range. The second data may be based at least in part on a decreased number of photons hitting the second photon detector 308 and a corresponding reduction in current generated by the second photon detector 308.

The operations may further include determining that a ratio of the first transmittance to the second transmittance corresponds to a transmittance ratio associated with a targeted gaseous chemical compound, which is methane in this example. The transmittance ratio of a first wavelength range of light to a second wavelength range of light may be gas dependent and/or wavelength range dependent. For example, the transmittance ratio of methane may differ from the transmittance ratio of other gaseous chemical compounds. To illustrate, methane may absorb infrared light at dominant absorption bands around 3020 $cm^{-1}$ and 1306 $cm^{-1}$. These dominant absorption bands may differ for gases other than methane. The transmittance ratio of light transmission at two dominant absorption bands may be, for example, 10:1, 9:1, 8:1, 7:1, 6:1, 5:1, 4:1, 3:1, or 2:1. While certain exemplary absorption bands are mentioned as relating to particular wavelengths, it should be appreciated that physical characteristics of the system will introduce certain variance. Based at least in part on this variance, the reference ratio may include a range of values that account for measurement tolerances.

The operations may further include determining that methane is the cause of light absorption based at least in part on determining that the detected ratio matches or substantially matches the transmittance ratio associated with methane. In examples, additional data, such as humidity data and temperature data may be utilized to compensate for humidity and temperature differences. In further examples, the operations may include determining the concentration of methane in the housing 302 using the transmittance data. Determining that methane is present in the housing 302 may be based at least in part on the concentration being at or above a threshold concentration. Determining the concentration of the detected gas may be determined using, for example, Beer's law along with known absorbance versus concentration data. For example, utilizing Beer's law, absorbance is equal to a molar extinction coefficient multiplied by the concentration and the path length. If absorbance is known, the equation can be solved for concentration by dividing absorbance by the product of the molar extinction coefficient and the path length. A line of best fit may be utilized to standardize concentration determinations on a standard linear curve. In examples, the transmittance data at a given absorption band may be utilized to determine concentration. The transmittance data from one of the dominant absorption bands may be used, and/or transmittance data from multiple dominant absorption bands may be used, and/or transmittance data from an absorption band and/or bands other than the dominant absorption bands may be used. In examples where transmittance data from multiple absorption bands are used, the determined concentration as between the multiple absorption bands may be compared and/or averaged to determine the concentration of the targeted gaseous chemical compound.

In the example provided with respect to FIG. 3, the computing components 310 may be part of the gas verification system and may be located at the environment that the gas is detected at. In other examples, some or all of the computing components 310 may be located at a remote location, such as remote system 318. As such, some or all of the operations described above with respect to FIG. 3 may be performed locally at the gas verification system or at the remote system 318.

While FIG. 3 depicts two LEDs, each of which having its own photon detector and cavity through which light from the LEDs travel, it should be understood that other configurations of LEDs, cavities, and photon detectors are contemplated by this disclosure to provide the functionality described herein. For example, the system 300 may include a single cavity with a single photon detector. In this example, the LEDs may be arranged to emit light in the same or a similar direction through the single cavity. The first LED may be enabled and the transmittance of light may be measured by the photon detector. Then, the second LED may be enabled and the transmittance of light may be measured by the same photon detector.

Although the placement of the various components of systems 200 and 300 are shown in FIGS. 2 and 3, respectively, in a specific order and/or at specific positions, it should be understood that other configurations of systems 200 and 300 may be utilized and one or more of the components shown in FIGS. 2 and/or 3 may not be utilized in these various configurations. By way of example, and not limitation, multiple LEDs may be disposed substantially adjacent to each other and directed in the same direction or similar directions. Light emitted from the LEDs may or may not pass through an optical filter and may be absorbed by one or more detectors. When an optical filter is utilized, it may be placed near the LEDs and/or near the one or more detectors. Additionally, or alternatively, one or more lenses may be utilized to focus the light emitted from the one or more light sources toward the one or more detectors. In other examples, such as when a single light source is utilized, the one or more detectors may be disposed at various angles with respect to the light source. For example, as shown in FIG. 2, the detectors are placed at approximately 180° from each other with respect to the light source. However, the detectors may be placed substantially next to each other or at various other angles from each other with respect to the light source.

Figure 4:
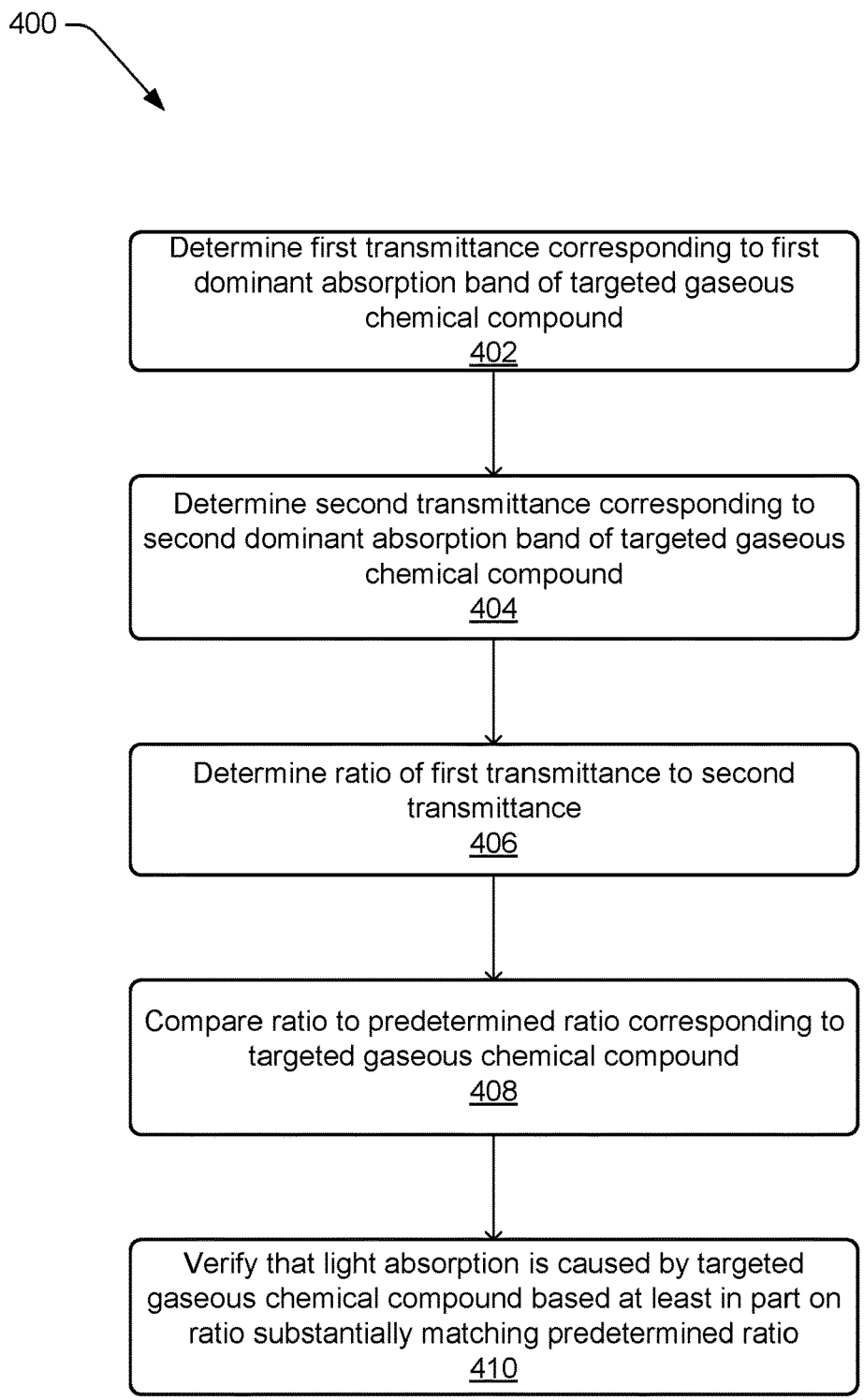
FIG. 4 illustrates a flow diagram of an example process for verifying that light absorption is caused by a targeted gaseous chemical compound.

FIG. 4 illustrates a flow diagram of an example process 400 for verifying that light absorption is caused by or is not caused by a targeted gaseous chemical compound. The order in which the operations or steps are described is not intended to be construed as a limitation, and any number of the described operations may be combined in any order and/or in parallel to implement process 400.

At block 402, the process 400 may include determining a first transmittance corresponding to a first dominant absorption band of a targeted gaseous chemical compound. A light may be received from a single light source, such as a light bulb containing a tungsten filament, or from multiple light sources, such as light emitting diodes (LEDs). When the light is received from a single light source, the light may be filtered using, for example, an optical filter. In this example, the optical filter may permit light at the first wavelength range to pass from the light source to the first photon detector while preventing light at other wavelengths from passing to the first photon detector. When the light is received from an LED, the LED may be configured to emit light at the first wavelength range. In this example, an optical filter may not be utilized. Photons of the light may hit the first photon detector, which may convert the photon measurement to current and/or a signal. That current or signal, representing at least a portion of the first data, may be transmitted to one or more processors for processing.

At block 404, the process 400 may include determining a second transmittance corresponding to a second dominant absorption band of the targeted gaseous chemical compound. In examples, when the light is received from a single light source, the light may be filtered using, for example, an optical filter. In other examples, when the light is received from an LED, the LED may be tuned to emit light at the second wavelength. Photons of the light may hit the second photon detector, which may convert the photon measurement to current and/or voltage, for example. That current and/or voltage may be transmitted, as at least a portion of the second data, to the one or more processors for processing.

At block 406, the process 400 may include determining a ratio of the first transmittance to the second transmittance. At block 408, the process 400 may include comparing the ratio to a predefined ratio corresponding to the targeted gaseous chemical compound. The transmittance ratio of a first dominant absorption band to a second dominant absorption band may be gas dependent and/or wavelength range dependent. For example, the transmittance ratio of methane may differ from the transmittance ratio of other gaseous chemical compounds. To illustrate, methane may absorb infrared light at dominant absorption bands around 3020 $cm^{-1}$ and 1306 $cm^{-1}$. These dominant absorption bands may differ for gases other than methane. The transmittance ratio of light transmission at two dominant absorption bands may be, for example, 10:1, 9:1, 8:1, 7:1, 6:1, 5:1, 4:1, 3:1, or 2:1. While certain exemplary absorption bands are mentioned as relating to particular wavelengths, it should be appreciated that physical characteristics of the system will introduce certain variance. Based at least in part on this variance, the reference ratio may include a range of values that account for measurement tolerances.

At block 410, the process 400 may include verifying that light absorption is caused by the targeted gaseous chemical compound based at least in part on the ratio substantially matching the predetermined ratio. This process may include accurately verify that the targeted gaseous chemical compound is present and other gases or conditions in the mixture are not affecting the verification/measurement of the targeted gaseous chemical compound. In examples, the detected ratio may match or substantially match a reference transmittance ratio of the targeted gaseous chemical compound. Data representing the transmittance ratio of the targeted gaseous chemical compound may be stored in memory and may be compared to the detected transmittance ratio verify that absorption is caused by the targeted gaseous chemical compound. Alternatively, the reference transmission ratios may be stored remote from the detection system and accessed via a wired or wireless network.

Additionally, transmittance data for gaseous water at least at the first and/or second wavelength ranges may be stored in the memory or otherwise accessed. The transmittance data for gaseous water, possibly based at least in part on humidity level and/or temperature, may be utilized to adjust the transmittance data from the first photon detector and/or the transmittance data from the second photon detector to compensate for humidity and/or temperature. In other examples, the transmittance data for gaseous water, which may be based at least in part on humidity level and/or temperature, may be utilized to modify the expected ratio for the targeted gaseous chemical compound. Additionally, or alternatively, the first wavelength range and/or the second wavelength range may be adjusted to differ from absorption ranges associated with water. For example, gaseous water may absorb light at the first and/or second wavelength ranges for a particular gaseous chemical compound. This absorption of light by the gaseous water may alter the detection of the target chemical compound from other compounds and/or cause a false reading. To overcome this potential issue, the absorption of light by the gaseous water may be attenuated or otherwise subtracted from transmittance data received from the first and/or second photon detectors. Additionally, or alternatively, the absorption of light by the gaseous water may be taken into account when determining the first and second wavelength ranges to examine to detect the target gaseous chemical compound. Techniques for normalizing readings of photon detectors to compensate for signal change due to absorption of light by gaseous water may be employed. In some examples, a humidity sensor and thermometer may be utilized to determine the amount of water molecules in the air mixture so that its effect on transmittance at both wavelengths can be taken into account.

In further examples, the operations may include determining the concentration of methane in the housing using the transmittance data and determining that methane is present in the housing may be based at least in part on the concentration being at or above a threshold concentration. In examples, some gaseous chemical compounds may be associated with a lower explosive limit and an upper explosive limit. The lower explosive limit may be the lowest concentration of gas or vapor in air capable of producing a flash fire in the presence of an ignition source. The lower explosive limit may also be described as the lower flammable limit. The upper explosive limit may be the highest concentration of a gas or vapor in air capable of producing a flash fire in the presence of an ignition source. In some examples, the threshold concentration at which it is determined that the gaseous chemical compound is present may be based at least in part on the lower explosive limit, the upper explosive limit, or a combination thereof.

The operations may further include causing one or more sound emitters to output an audible alarm based at least in part on verifying that light absorption is caused by the targeted gaseous chemical compound. The audible alarm may provide an indication to people within hearing distance of the device that a hazardous or unwanted gas has been detected and that the environment is dangerous. In some examples, the audible alarm may include one or more loud noises. The audible alarm may, additionally or alternatively, include synthesized and/or prerecorded speech that notifies people within hearing distance that a hazardous or unwanted gas has been detected. In these examples, the audio may also provide instructions for how to proceed, such as an instruction to evacuate the area, call authorities for assistance, and/or instructions for how to mitigate a gas leak such as, for example, by turning the flow of a gas off.

The operations may additionally, or alternatively, include sending message data to a device, such as a mobile device. The message data may provide a notification to a user of the device that a hazardous or unwanted gas has been identified at the gas verification system. The notification may provide textual or audible information related to the verification of the presence of the gas. The operations may additionally, or alternatively, include sending data to the remote system and/or other systems indicating that the gas has been identified. This information may be utilized to contact authorities, remotely shut off flow of gas to the environment where the gas was detected, and/or estimate the impact of the detected gas to, for example, humans within a certain distance of the gas detector.

In some examples, transmittance of light at a third wavelength range may be determined and data corresponding to the transmittance of light at the third wavelength range may be used to verify that light absorption is caused by a target gaseous chemical compound. For example, in instances where the system includes a single light source, a third optical filter may be utilized and configured to permit light at a third wavelength range to pass from the light source to a photon detector, which may measure transmittance of the light. In instances where the verification system includes LED light sources, a third LED tuned to emit the third wavelength range of light may be utilized. The third transmittance data may be utilized along with the first transmittance data and/or the second transmittance data to verify that light absorption is caused by the targeted gaseous chemical compound. For example, a ratio of the first transmittance to the third transmittance may be utilized. Additionally, or alternatively, a ratio of the second transmittance to the third transmittance may be utilized. In these examples, these ratios may be compared to known ratios associated with the targeted gaseous chemical compound to verify the presence or absence of the targeted gaseous chemical compound. In other examples, a ratio including each of the three transmittances may be utilized (e.g., 3:1:1) and compared to known ratios of the targeted gaseous chemical compound. Additional wavelength ranges of light may be monitored to further assist in verifying that light absorption is caused by the targeted gaseous chemical compound and/or other gases.

In examples, the system performing process 400 may be powered by a battery and may, or may not, be connected to a power source other than the battery. In these or other examples, the system may be a component of a meter or other device that is powered via electricity supplied at the environment at which the system is disposed. In other examples, a portion of the components of the system 400 may be powered by a power source local to the system 400, such as a battery, while other components of the system 400 may be powered remotely.

Figure 5:
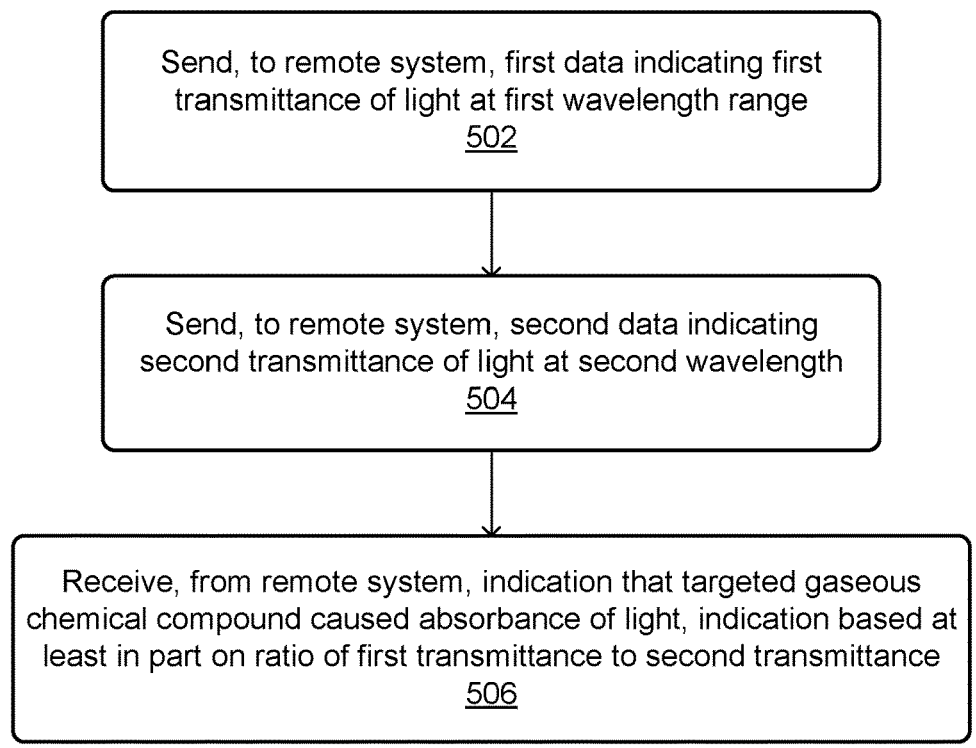
FIG. 5 illustrates a flow diagram of another example process for verifying that light absorption is caused by a targeted gaseous chemical compound.

FIG. 5 illustrates a flow diagram of an example process 500 for detecting a gaseous chemical compound. The order in which the operations or steps are described is not intended to be construed as a limitation, and any number of the described operations may be combined in any order and/or in parallel to implement process 500.

At block 502, the process 500 may include sending, from a light detector to a remote system, first data indicating a first transmittance of light at a first wavelength range. The light may be produced by a single light source, such as a light bulb containing a tungsten filament, or from multiple light sources, such as light emitting diodes (LEDs). When the light is produced from a single light source, the light may be filtered using, for example, an optical filter. The optical filter may permit light at the first wavelength range to pass from the light source to the photon detector while preventing light at other wavelengths from passing to the photon detector. When the light is produced by an LED, the LED may be tuned or configured to emit light at the first wavelength range. In this example, an optical filter may not be utilized.

Photons of the light may hit the light detector, which may convert the photon measurement to current and/or signal. That current or signal may be sent, as at least a portion of the first data, to the remote system. In examples, there may be two or more light detectors and each of the light detectors may be configured to receive light at a given wavelength range. Additionally, or alternatively, there may be multiple light sources and each of the light sources may be configured to produce light in a certain wavelength range. Additionally, or alternatively, there may be multiple optical filters that may allow certain wavelength ranges of light to pass from the light source(s) to the light detector(s).

At block 504, the process 500 may include sending, to the remote system, second data indicating a second transmittance of light at the second wavelength range. When the light is produced by a single light source, the light may be filtered using, for example, an optical filter. When the light associated with the photon detector is produced by an LED, the LED may be tuned or configured to emit light at the second wavelength. Photons of the light may hit the photon detector, which may convert the photon measurement to current. That current may be sent, as at least a portion of the second data, to the remote system.

At block 506, the process 500 may include receiving, from the remote system, an indication that a targeted gaseous chemical compound caused absorbance of the light. The indication may be based at least in part on a ratio of the first transmittance to the second transmittance corresponding to a transmittance ratio associated with the targeted gaseous chemical compound. The transmittance ratio of a first wavelength range of light to a second wavelength range of light may be gas dependent and/or wavelength range dependent. For example, the transmittance ratio of methane may differ from the transmittance ratio of other gaseous chemical compounds. To illustrate, methane may absorb infrared light at dominant absorption bands around 3020 $cm^{-1}$ and 1306 $cm^{-1}$. These dominant absorption bands may differ for gases other than methane. It should be noted that while specific dominant absorption bands are provided here as illustration, the absorption bands may include a range of absorption bands that include absorption bands that are slightly greater than and/or slightly less than the noted dominant absorption band. Additionally, depending on the concentration of methane, the transmittance and absorption of light may vary. For example, when a relatively low concentration of methane is present, absorption at the dominant absorption bands will be less than absorption at relatively high concentrations of methane. One or more reference ratios for a targeted gaseous chemical compound, such as, for example, methane, may be stored or otherwise accessed and compared with the measured transmittance ratio.

The remote system may verify that light absorbance is caused by the targeted gaseous chemical compound based at least in part on the detected ratio corresponding to the transmittance ratio (of two particular wavelength ranges) associated with the targeted gaseous chemical compound. In examples, the detected ratio may match or substantially match a known transmittance ratio of the targeted gaseous chemical compound. Data representing the transmittance ratio of the targeted gaseous chemical compound at given wavelength ranges may be stored in memory and/or stored remotely and accessed by the system and may be compared to the detected transmittance ratio to determine whether the detected transmittance of light at the first and second wavelength ranges corresponds to detection of the gaseous chemical compound.

Additionally, transmittance data for gaseous water at least at the first and/or second wavelength ranges may be stored in the memory. The transmittance data for gaseous water may be utilized to modify the transmittance data from the photon detector. For example, gaseous water may absorb light at the first and/or second wavelength ranges at the same time that a particular gaseous chemical compound. This absorption of light by the gaseous water may result in different absorption levels in several wavelength ranges, and thereby alter the differentiation of the chemical compound and/or cause a false reading. To overcome this potential issue, the absorption of light by the gaseous water may be compensated for or otherwise subtracted from transmittance data received from the photon detector. In some examples, a humidity sensor may be utilized to determine the amount of absorption being caused by the gaseous water. In further examples, a temperature sensor may be utilized to determine a temperature of gas molecules being measured. The temperature data may also be utilized to determine an amount of interference being caused by variances in temperature.

In further examples, the remote system may determine the concentration of the gas in the housing using the transmittance data and determine that the gas is present in the housing may be based at least in part on the concentration being at or above a threshold concentration. In examples, some gaseous chemical compounds may be associated with a lower explosive limit and an upper explosive limit. The lower explosive limit may be the lowest concentration of gas or vapor in air capable of producing a flash fire in the presence of an ignition source. The lower explosive limit may also be described as the lower flammable limit. The upper explosive limit may be the highest concentration of a gas or vapor in air capable of producing a flash fire in the presence of an ignition source. In some examples, the threshold concentration at which it is determined that the gaseous chemical compound is present may be based at least in part on the lower explosive limit, the upper explosive limit, or a combination thereof.

Figure 6:
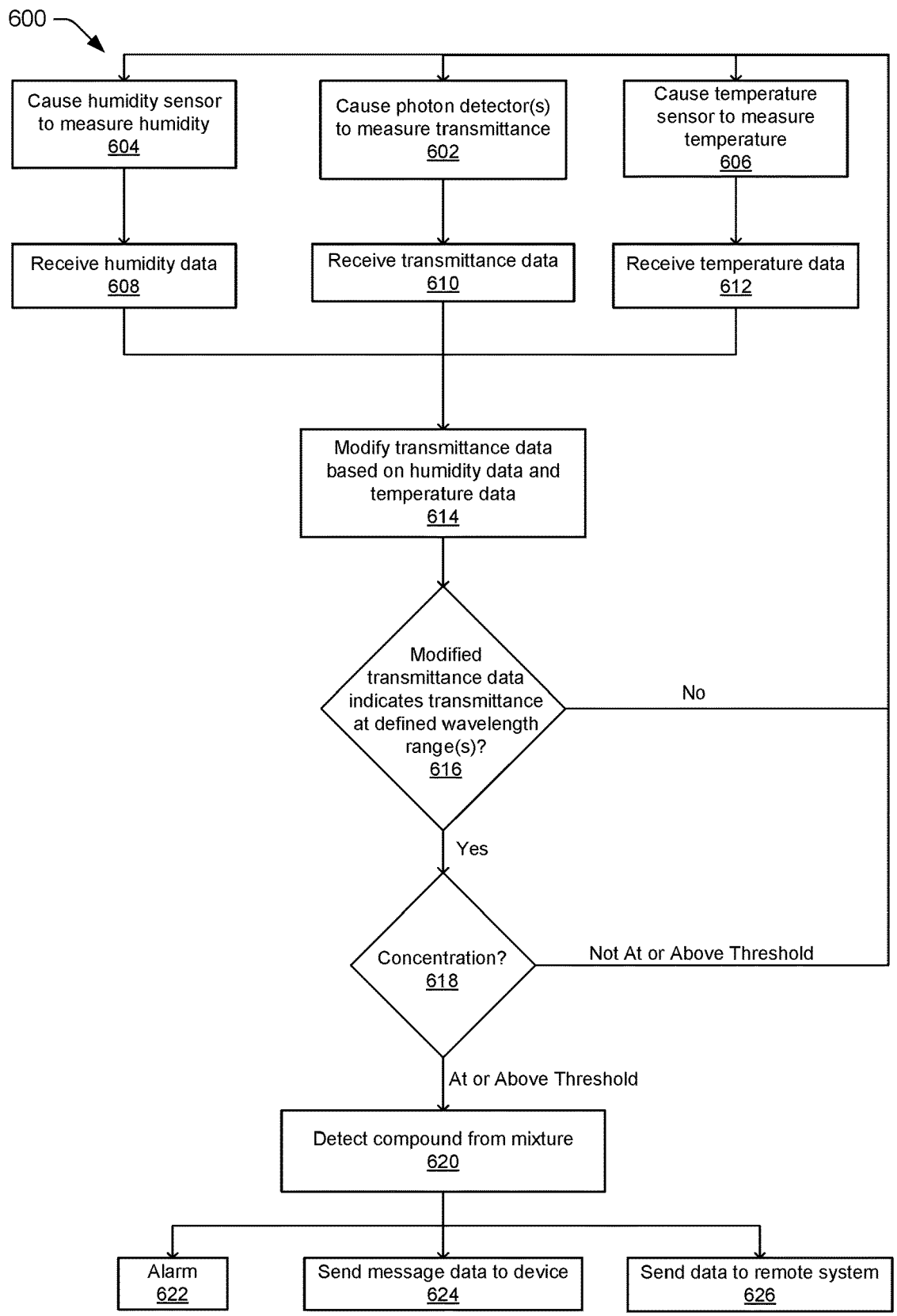
FIG. 6 illustrates a flow diagram of another example process for verifying that detected absorption of light is caused primarily by a targeted gaseous chemical compound.

FIG. 6 illustrates a flow diagram of another example process 600 for detecting a gaseous chemical compound. The process 600 provides several operations and determinations for verifying that light absorption is caused by or is not caused by a targeted gaseous chemical compound.

At block 602, the process 600 may include causing two or more photon detectors to measure transmittance of light. Causing the photon detectors to measure transmittance of light may include continually causing the photon detectors to generate current, or result in a signal, corresponding to quantities of photons hitting the photon detectors. Causing the photon detectors to measure transmittance of light may alternatively include periodically causing the photon detectors to generate current corresponding to photons hitting the photon detectors.

At block 604, the process 600 may include causing a humidity sensor to measure humidity. Causing the humidity sensor to measure humidity may be performed continuously, periodically, and/or at a rate comparable to the rate of transmittance measurement from the photon detectors.

At block 606, the process 600 may include causing a temperature sensor to measure temperature. Causing the temperature sensor to measure temperature may be performed continuously, periodically, and/or at a rate comparable to the rate of transmittance measurement from the photon detectors and/or at a rate comparable to rate of humidity measurement from the humidity sensor.

At block 608, the process 600 may include receiving humidity data corresponding to the humidity measured by the humidity sensor. At block 610, the process 600 may include receiving transmittance data corresponding to the transmittance of light measured by the photon detectors. At block 612, the process 600 may include receiving temperature data corresponding to the temperature measured by the temperature sensor.

At block 614, the process 600 may include modifying, adjusting and/or refining the transmittance data based on the humidity data and/or the temperature data. As an example, the refined data better excludes the misleading effect of light absorption by gaseous water, and tends to clarify absorption attributed to a gas, such as methane, propane, etc. For example, measured light transmission values may be adjusted based at least in part on light absorption by gaseous water to a degree proportional to the humidity measured at block 604 and temperature measured by block 606. Additionally, temperature variations that may alter the transmittance of light as measured by the photon detectors may be taken into account.

At block 616, the process 600 may include determining whether the modified transmittance data indicates absorption at defined wavelength ranges corresponding to the targeted gaseous chemical compound. If the modified transmittance data does not indicate transmittance at the defined wavelength ranges, the process 600 may return to blocks 602, 604, and/or 606. If the modified transmittance data indicates absorption at the defined wavelength ranges, the process 600 may continue to block 618 where a determination may be made as to whether a concentration of the gaseous chemical compound is at or above a threshold concentration. The concentration of the detected gas may be determined based at least in part on the percent transmittance as measured by the photon detectors. Determining the concentration of the detected gas may be determined using, for example, Beer's law along with known absorbance versus concentration data. For example, utilizing Beer's law, absorbance is equal to a molar extinction coefficient multiplied by the concentration and the path length. If absorbance is known, the equation can be solved for concentration by dividing absorbance by the product of the molar extinction coefficient and the path length. A line of best fit may be utilized to standardize concentration determinations on a standard linear curve. Once absorbance and known concentrations are correlated such that data is generated that identifies concentrations at various absorbances, the percent transmittance can be converted to absorbance, which may be compared to the data to identify the corresponding concentration.

If the detected concentration is not at or above the threshold concentration, the process 600 may return to blocks 602, 604, and/or 606. If the detected concentration is at or above the threshold concentration, the process 600 may continue to block 620 where it may be determined that the gaseous chemical compound is present at least at a level determined to be potentially hazardous or unwanted.

At block 622, the process 600 may include causing one or more sound emitters to output an audible alarm. The audible alarm may provide an indication to people within hearing distance of the device that a hazardous or unwanted gas has been detected and that the environment is dangerous. In some examples, the audible alarm may include one or more loud noises. The audible alarm may, additionally or alternatively, include synthesized and/or prerecorded speech that notifies people within hearing distance that a hazardous or unwanted gas has been detected. In these examples, the audio may also provide instructions for how to proceed, such as an instruction to evacuate the area, call authorities for assistance, and/or instructions for how to mitigate a gas leak such as, for example, by turning the flow of a gas off.

At block 624, the process 600 may include sending message data to a device, such as a mobile device. The message data may provide a notification to a user of the device that a hazardous or unwanted gas has been identified at the gas verification system. The notification may provide textual or audible information related to the detection of the gas.

At block 626, the process 600 may include sending data to a remote system and/or other systems indicating that the gas has been detected. This information may be utilized to contact authorities, remotely shut off flow of gas to the environment where the gas was detected, and/or measure impact of the detected gas.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention. For example, while several of the examples provided above have described a gas detection system configured to detect a specific gaseous chemical compound, it should be understood that the gas detection systems described herein may be configured to detect two or more gaseous chemical compounds.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A method comprising:
   receiving data indicating:
      a first transmittance of first light at a first wavelength range through a gas; and
      a second transmittance of second light at a second wavelength range through the gas;
   determining a ratio of the first transmittance to the second transmittance;
   comparing the ratio to a reference ratio associated with a reference gas;
   identifying the gas as containing at least the reference gas based at least in part on the comparing; and
   outputting an alarm based at least in part on identifying the gas as containing at least the reference gas.

2. The method of claim 1, wherein the reference gas is methane.

3. The method of claim 1, further comprising:
   determining, based at least in part on at least one of the first transmittance or the second transmittance, a concentration of the gas; and
   wherein identifying the gas as containing at least the reference gas is based at least in part on the concentration.

4. The method of claim 1, wherein the data comprises first data, and the method further comprises:
   accessing at least a portion of second data indicating light transmittance through gaseous water at the first wavelength range and the second wavelength range; and
   modifying the first data based at least in part on the second data.

5. The method of claim 1, further comprising sending, to a mobile device, message data based at least in part on identifying the gas as containing at least the reference gas, the message data including at least one of audio data or text data indicating that the gas is present at a location.

6. The method of claim 1, wherein the data comprises first data, and the method further comprises:
receiving second data indicating a third transmittance of third light at a third wavelength range; and
wherein identifying the gas as containing at least the reference gas is based at least in part on the second data.

7. The method of claim 1, wherein the alarm is an audible alarm.

8. The method of claim 1, further comprising:
adjusting the received data based at least in part on second data received from at least one of a humidity sensor or a temperature sensor.

9. A system comprising:
a light source that produces light;
a light detector;
one or more processors; and
non-transitory computer-readable media storing instructions that, when executed by the one or more processors, cause the one or more processors to perform operations comprising:
sending first data indicating a first transmittance of the light at a first wavelength range;
sending second data indicating a second transmittance of the light at a second wavelength range;
receiving an indication that a gas contains at least a reference gas, the indication based at least in part on a ratio of the first transmittance to the second transmittance; and
adjusting at least one of the first data or the second data based at least in part on third data received from at least one of a humidity sensor or a temperature sensor.

10. The system of claim 9, wherein the reference gas is methane.

11. The system of claim 9, further comprising:
a first optical filter tuned to transmit the first wavelength range of the light; and
a second optical filter tuned to transmit the second wavelength range of the light.

12. The system of claim 9, wherein the light detector comprises a first light detector, and further comprising a second light detector, the first light detector configured to receive the light at the first wavelength range and the second light detector configured to receive the light at the second wavelength range.

13. The system of claim 9, wherein the first wavelength range is about 3010 $cm^{-1}$ to about 3025 $cm^{-1}$ and the second wavelength range is about 1300 $cm^{-1}$ to about 1315 $cm^{-1}$.

14. The system of claim 9, wherein the light source comprises a first light source configured to emit the light at the first wavelength range, and further comprising a second light source configured to emit the light at the second wavelength range.

15. The system of claim 9, the operations further comprising:
sending third data indicating a third transmittance of the light at a third wavelength range; and
wherein the indication that the gas contains at least the reference gas is based at least in part on the third data.

16. The system of claim 9, wherein the indication is based at least in part on third data received from at least one additional gas detection system.

17. A system comprising:
one or more processors; and
non-transitory computer-readable media storing instructions that, when executed by the one or more processors, cause the one or more processors to perform operations comprising:
receiving data indicating:
a first transmittance of first light at a first wavelength range through a gas; and
a second transmittance of second light at a second wavelength range through the gas;
determining a ratio of the first transmittance to the second transmittance;
comparing the ratio to a reference ratio associated with a reference gas;
identifying the gas as containing at least the reference gas based at least in part on the comparing; and
adjusting the received data based at least in part on second data received from at least one of a humidity sensor or a temperature sensor.

18. The system of claim 17, the operations further comprising:
determining, based at least in part on at least one of the first transmittance or the second transmittance, a concentration of the gas; and
wherein identifying the gas as containing at least the reference gas is based at least in part on the concentration.

19. The system of claim 17, wherein the data comprises first data, and the operations further comprise:
accessing at least a portion of second data indicating light transmittance through gaseous water at the first wavelength range and the second wavelength range; and
modifying the first data based at least in part on the second data.

20. The system of claim 17, the operations further comprising sending, to a mobile device, message data based at least in part on identifying the gas as containing at least the reference gas, the message data including at least one of audio data or text data indicating that the gas is present at a location.

* * * * *